(12) United States Patent
Galotta et al.

(10) Patent No.: US 10,591,447 B2
(45) Date of Patent: Mar. 17, 2020

(54) ELEMENTAL ANALYZER USING CARRIER GAS SUPPLIER

(71) Applicant: Thermo Fisher Scientific S.p.A., Milan (IT)

(72) Inventors: Walter Galotta, Milan (IT); Andrea Magni, Milan (IT); Liliana Krotz, Milan (IT); Francesco Leone, Milan (IT)

(73) Assignee: Thermo Fisher Scientific S.P.A, Milan (IT)

( * ) Notice: Subject to any disclaimer, the term of this patent is extended or adjusted under 35 U.S.C. 154(b) by 79 days.

(21) Appl. No.: 15/726,279

(22) Filed: Oct. 5, 2017

(65) Prior Publication Data

US 2018/0100838 A1  Apr. 12, 2018

(30) Foreign Application Priority Data

Oct. 10, 2016 (EP) .................................... 16425096

(51) Int. Cl.
| | | |
|---|---|---|
| *G01N 30/66* | (2006.01) | |
| *G01N 31/12* | (2006.01) | |
| *G01N 30/20* | (2006.01) | |
| *G01N 30/02* | (2006.01) | |
| G01N 30/84 | (2006.01) | |

(52) U.S. Cl.
CPC ............ *G01N 30/66* (2013.01); *G01N 30/02* (2013.01); *G01N 30/20* (2013.01); *G01N 31/12* (2013.01); G01N 2030/025 (2013.01); G01N 2030/8405 (2013.01)

(58) Field of Classification Search
CPC ........ G01N 30/66; G01N 30/02; G01N 30/20; G01N 30/72; G01N 30/12; G01N 2030/025; G01N 2030/8405; G01N 25/26; G02N 31/12
See application file for complete search history.

(56) References Cited

U.S. PATENT DOCUMENTS

| | | | | |
|---|---|---|---|---|
| 6,653,143 B2 * | 11/2003 | Ragaglia | ............... | G01N 31/12 422/78 |
| 2010/0212398 A1 * | 8/2010 | Krummen | ............... | G01N 1/28 73/23.37 |
| 2011/0308298 A1 * | 12/2011 | Magni | ................... | G01N 30/32 73/23.35 |

FOREIGN PATENT DOCUMENTS

| | | |
|---|---|---|
| CN | 201780284 U | 3/2011 |
| EP | 0940677 B1 | 9/2002 |
| EP | 1061366 B1 | 1/2007 |

* cited by examiner

*Primary Examiner* — Harshad R Patel
*Assistant Examiner* — Nigel H Plumb (57) ABSTRACT

An analysis system for analysing the constituents of a sample of material is provided. A reference supply conduit supplies a source of a first gas. A carrier supply conduit supplies a source of the first or a second gas. First and second reactors are included. A first auto-sampler provides one or more samples of material, the first auto-sampler having an inlet for receiving gas and an outlet for providing the received gas and a sample to the first reactor. A second auto-sampler provides one or more samples of material, the second auto-sampler having an inlet for receiving gas and an outlet for providing the received gas and a sample to the second reactor. A thermal conductivity detector has first and second channels for identifying the relative conductivity of the gases in each channel. A valve system controls the flow of gas from the supply conduits to the auto-samplers.

15 Claims, 10 Drawing Sheets

FIG. 4A
CHN-CHN Configuration

ELEMENTAL ANALYZER USING CARRIER GAS SUPPLIER

CROSS-REFERENCE TO RELATED APPLICATION

This application claims the priority benefit under 35 U.S.C. § 119 to European Patent Application No. 16425096.1, filed on Oct. 10, 2016, the disclosure of which is incorporated herein by reference.

FIELD OF THE INVENTION

The invention relates to elemental analyzers and, in particular, but not exclusively, organic elemental analyzers and isotope ratio mass spectrometry (IRMS) elemental analyzers.

BACKGROUND OF THE INVENTION

Organic elemental analyzers are known, for example the Flash 2000 Elemental Analyzer manufactured by Thermo Scientific. In these devices, a thermal conductivity detector is used to compare the conductivity of a portion of the reaction products of a sample material (which passes along a "measurement" channel of the thermal conductivity detector (TCD)) with the conductivity of a reference gas (which passes along a "reference" channel of the thermal conductivity detector). Also known are isotope ratio mass spectrometry (IRMS) elemental analyzers, for example the EA IsoLink IRMS System, which includes the Flash IRMS Elemental Analyzer manufactured by Thermo Scientific. In the EA IsoLink IRMS System, a mass spectrometer is used to measure the isotope ratio of an element in the reaction products of a sample material. The invention will be described primarily in the context of an organic elemental analyzer but it should be understood that the invention is also applicable to elemental analyzers interfaced with IRMS.

The sample of material is provided by an auto-sampler, which can be loaded with multiple samples of one or more material and delivers these into a reactor to undergo reaction. It is important that the sample is not contaminated and so the auto-sampler is supplied with a carrier gas, and the sample material is delivered into the reactor in the presence of the carrier gas. The reactor can be a combustion reactor, combustion/reduction reactor or pyrolysis reactor for example. The products of the reaction, for example $CO_2$, $CO$, $NO_x$, $N_2$, $H_2$, $H_2O$, and/or $SO_2$, along with the carrier gas are then fed to the measurement channel of the thermal conductivity detector. A reference gas, which may be the same as the carrier gas, is conveyed to the reference channel of the thermal conductivity detector. In this way the amount of reaction products can be measured and hence an elemental content (for example the content of one or more of C, H, N, S and/or O) can be determined. In the case of an IRMS elemental analyzer, the reaction products can be ionised downstream of the reactor (optionally downstream of the TCD where present) and thereafter mass analysed to determine an isotope ratio of one or more reaction products.

To further avoid contamination, it is necessary that the system remains continually supplied with the carrier gas to prevent the contamination of any future experiments with environmental gases.

Typically, other devices will be provided between the reactor and the thermal conductivity detector. For example, the output of the reactor may pass to an adsorption (or absorption) trap for the removal of particular species from the gas stream, for example water, as required by the particular analysis being performed and from there to a separation device such as a chromatography column to separate the reaction products thereby allowing them to pass sequentially to the thermal conductivity detector.

Such systems may be configured for "CHNS determination" (carbon, hydrogen, nitrogen, sulphur) or "O determination" (oxygen). In this context, "CHNS determination" includes any determination of any subset of these elements such as CHN or NCS determinations for example. In each of these configurations, the system requires a different configuration and may use different carrier and reference gases.

It is problematic to re-configure existing systems, which are not flexible and do not allow a variety of different analyses to be scheduled in advance. Consequently, this requires hardware modifications that are time-consuming and reduce the operation time of the instrument and thus reduces significantly laboratory throughput and instrument automation. Moreover, the requirement for a continuous supply of carrier gas when the device is not in use is costly and increasingly problematic in light of the global helium supply shortage relative to very high demand.

There is therefore a need to overcome these disadvantages and provide a more flexible, automated system that may increase sample throughput, may reduce maintenance intervals and may increase automation.

SUMMARY

According to a first aspect of the invention, there is provided an analysis system for analysing the constituents of a sample of material, the system comprising: a reference supply conduit for supplying a source of a first gas; a carrier supply conduit for supplying a source of the first or a second gas; first and second reactors; a first auto-sampler for providing one or more samples of material, the first auto-sampler having an inlet for receiving gas and an outlet for providing the received gas and a sample to the first reactor; a second auto-sampler for providing one or more samples of material, the second auto-sampler having an inlet for receiving gas and an outlet for providing the received gas and a sample to the second reactor; and a thermal conductivity detector having first and second channels for identifying the relative conductivity of the gases in each channel.

The system also comprises a valve system arranged to control the flow of gas from the supply conduits to the inlets of the first and second auto-samplers.

The analysis system has a first mode of operation in which: the valve system connects the carrier supply conduit with the first auto-sampler; the first auto-sampler delivers the received gas and a sample to the first reactor; the first reactor delivers a reaction product to one channel of the thermal conductivity detector; and the valve system connects the reference supply conduit to the other channel of the thermal conductivity detector.

The analysis system has a second mode of operation in which: the valve system connects the carrier supply conduit with the second auto-sampler; the second auto-sampler delivers the received gas and a sample to the second reactor; the second reactor delivers a reaction product to one channel of the thermal conductivity detector; and the valve system connects the reference supply conduit to the other channel of the thermal conductivity detector.

According to a second aspect of the invention, there is provided an analysis system for analysing the constituents of a sample of material, the system comprising: a reference supply conduit for supplying a source of a first gas; a carrier supply conduit for supplying a source of the first or a second gas; a stand-by supply conduit for supplying a source of a stand-by gas; a reactor; an auto-sampler for providing one or more samples of material, the auto-sampler having an inlet for receiving gas and an outlet for providing the received gas and a sample to the reactor; and a thermal conductivity detector having first and second channels for identifying the relative conductivity of the gases in each channel, wherein: the system also comprises a valve system arranged to control the flow of gas from the supply conduits to the inlet of the auto-sampler; the analysis system has a normal mode of operation in which: the valve system connects the carrier supply conduit with the auto-sampler; the auto-sampler delivers the received gas and a sample to the reactor; the reactor delivers a reaction product to one channel of the thermal conductivity detector; and the valve system connects the reference supply conduit to the other channel of the thermal conductivity detector; and the analysis system has a stand-by mode of operation in which: the valve system connects the stand-by supply conduit with the auto-sampler; the auto-sampler delivers the received gas to the reactor without delivering a sample; the reactor delivers the received gas substantially unchanged to one channel of the thermal conductivity detector; and the valve system connects the stand-by supply conduit to the other channel of the thermal conductivity detector.

According to a third aspect of the invention, there is provided an analysis system for analysing the constituents of a sample of material, the system comprising:

a reference supply conduit for supplying a source of a first gas;

a carrier supply conduit for supplying a source of the first or a second gas;

first and second reactors;

a first auto-sampler for providing one or more samples of material, the first auto-sampler having an inlet for receiving gas and an outlet for providing the received gas and a sample to the first reactor;

a second auto-sampler for providing one or more samples of material, the second auto-sampler having an inlet for receiving gas and an outlet for providing the received gas and a sample to the second reactor;

a thermal conductivity detector (10) having first and second channels for identifying the relative conductivity of the gases in each channel, wherein a valve system (80, 100, 200) is arranged to:

connect the output of the first reactor (30*a*) to a first of the channels of the thermal conductivity detector (10) and simultaneously connect the output of the second reactor (30*b*) to a second of the channels of the thermal conductivity detector (10); or connect the output of the first reactor (30*a*) to the second of the channels of the thermal conductivity detector (10) and simultaneously connect the output of the second reactor (30*b*) to the first of the channels of the thermal conductivity detector (10).

In this third aspect, it is preferable that: more than two reactors (30) are provided; the valve system (80, 100) is arranged to connect the carrier supply conduit to at least one of the reactors (30) and connect the at least one of the reactors (30) with a first of the channels of the thermal conductivity detector (10); and the valve system (80, 100, 200) is arranged to connect the reference supply conduit to the other reactors (30) and connect those other reactors (30) with a second of the channels of the thermal conductivity detector (10).

In this third aspect, it is preferable that: more than two auto-samplers (20) are provided; the valve system (80, 100, 200) is arranged to connect the carrier supply conduit to at least one of the auto-samplers (20) and connect the at least one of the auto-samplers (20) with a first of the channels of the thermal conductivity detector (10) via a reactor 30; and the valve system (80, 100, 200) is arranged to connect the reference supply conduit to the other auto-samplers (20) and connect those other auto-samplers (20) with a second of the channels of the thermal conductivity detector (10) via a reactor 30.

BRIEF DESCRIPTION OF THE DRAWINGS

For a better understanding of the invention and to show how the same may be put into effect, reference is now made, by way of example only, to the accompanying drawings in which:

FIG. 2, comprised of FIGS. 2A-C, show a schematic depicting a preferred embodiment of an elemental analyzer in accordance with the invention;

DETAILED DESCRIPTION OF EMBODIMENTS

Figure 1:
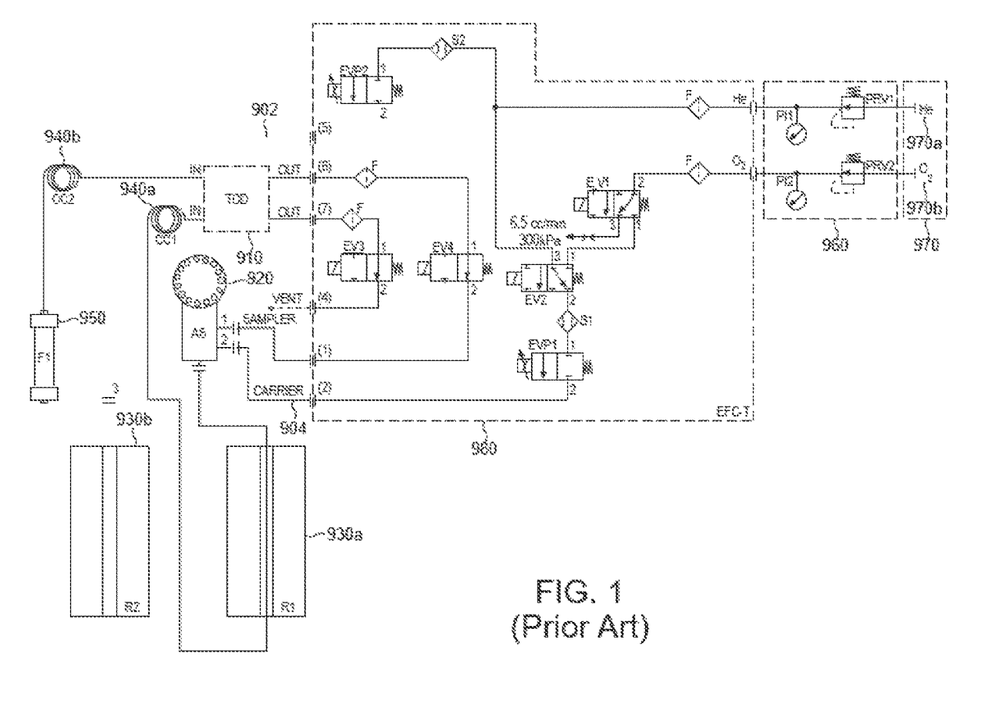
FIG. 1 shows a schematic depicting a prior art elemental analyzer.

As can be seen from FIG. 1, a prior art elemental analyzer comprises: a thermal conductivity detector 910; two chromatography columns 940*a*, 940*b*; an absorption trap 950; two reactors 930*a*, 930*b*; an auto-sampler 920; a pressure regulator 960, a supply valve system 980, and a source of gases 970, such as helium 970*a* and oxygen 970*b*.

Figures 2, 2A:
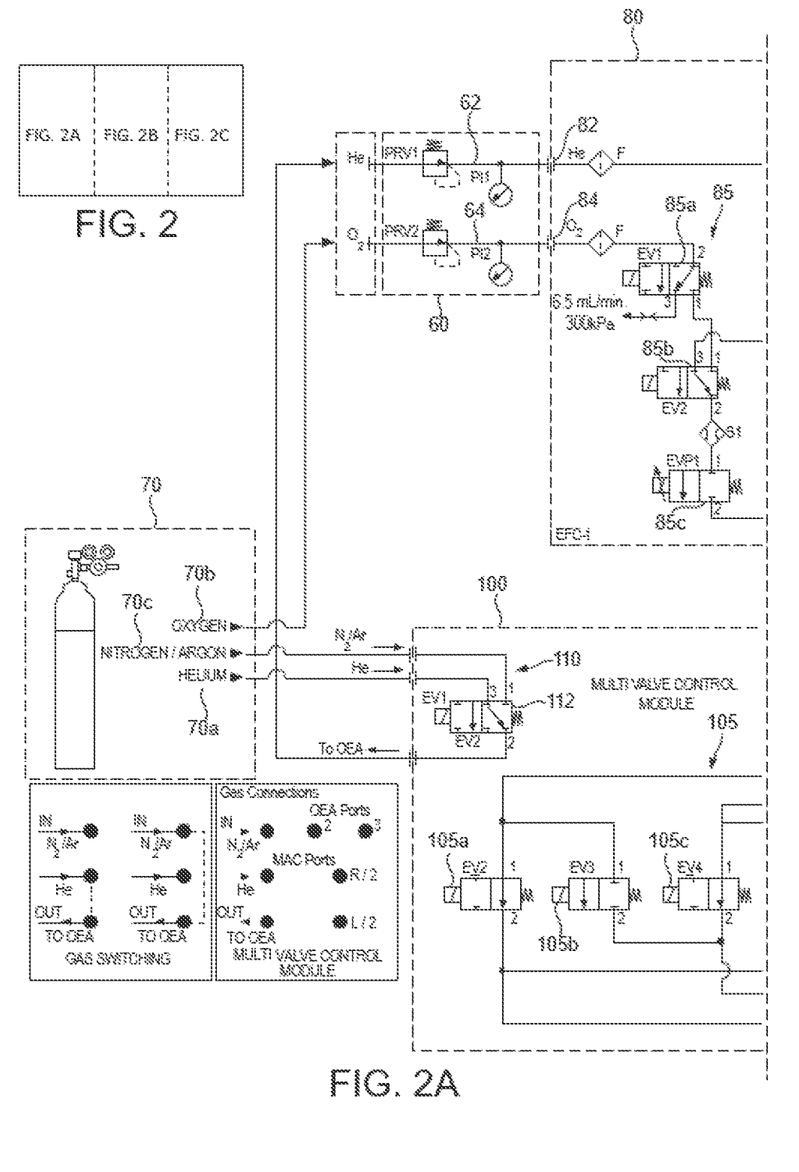
Figure 2B:
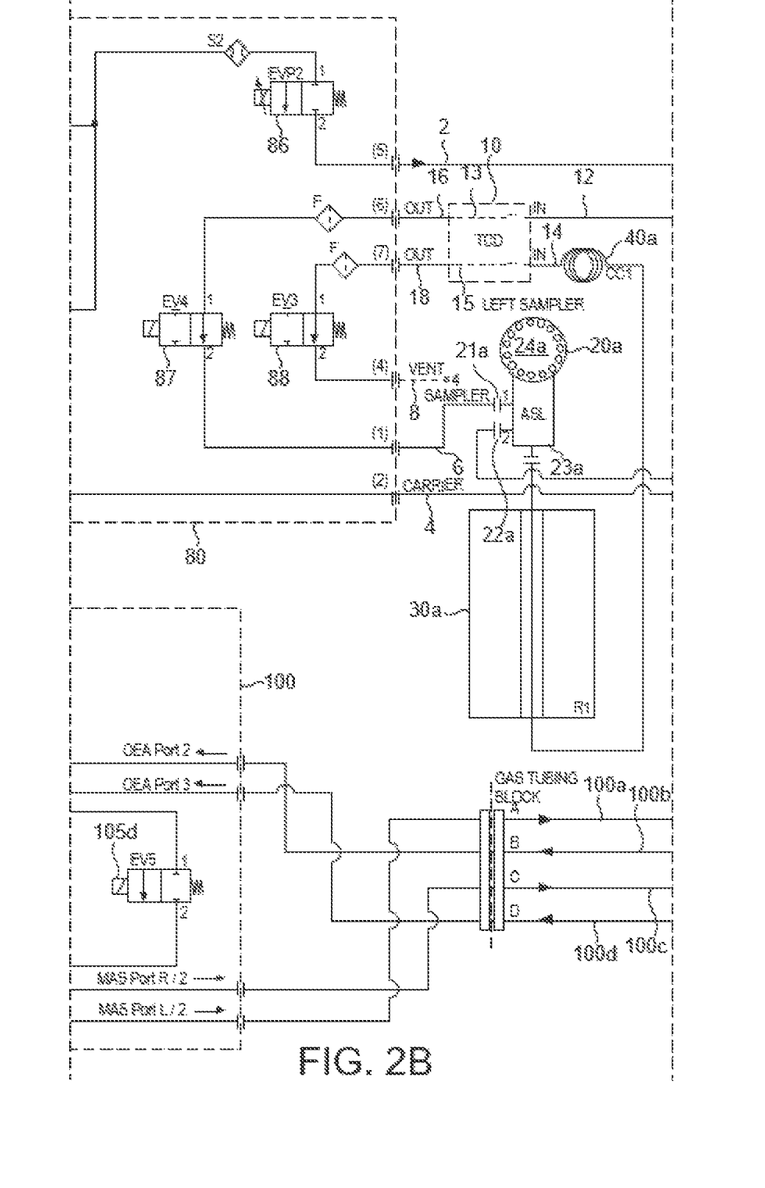
Figure 2C:
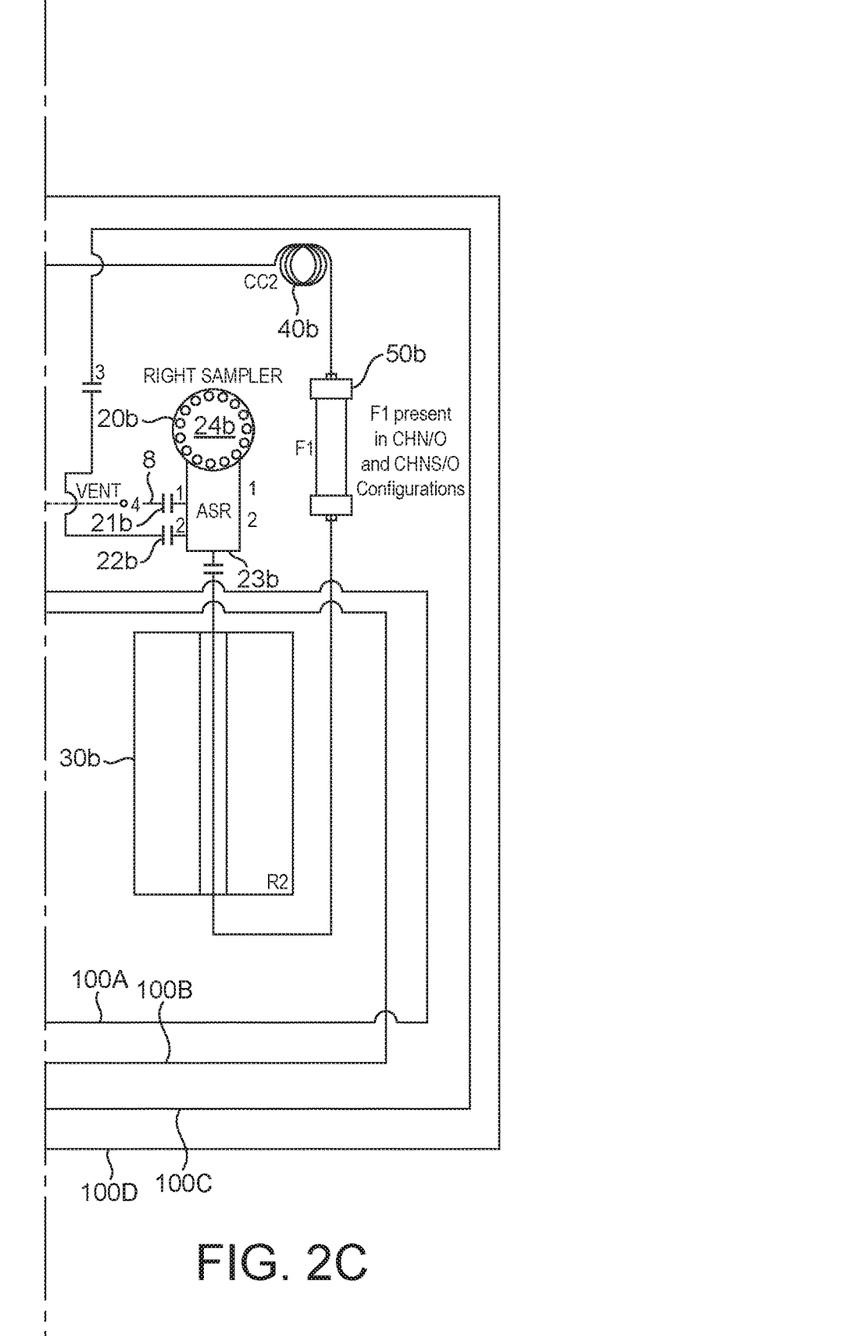

FIGS. 2A-C show a preferred embodiment of an elemental analyzer in accordance with the invention. The elemental analyzer may be an organic elemental analyzer.

The preferred elemental analyzer comprises: a valve system 80, 100; a thermal conductivity detector 10; two chromatography columns 40*a*, 40*b*; an adsorption (or absorption) trap 50*b*; two reactors 30*a*, 30*b*; two auto-samplers 20*a*, 20*b*; and a source of gases 70.

An element analyzer 1 (see FIG. 3) comprises the thermal conductivity detector 10; the chromatography columns 40*a*, 40*b*; the adsorption (or absorption) trap 50*b*; the two reactors 30*a*, 30*b*; and the two auto-samplers 20.

As is known in the art, the chromatography columns 40*a*, 40*b* are suitable for separating constituents of a flow of gas, and the adsorption (or absorption) trap 50*b* is suitable for removing certain components (in particular, water vapour) from a gas flow.

In the preferred embodiment shown in FIGS. 2A-C, one of the reactors 30*a*, 30*b* is of a combustion/reduction type (for CHNS determination) and the other of the reactors 30*a*, 30*b* is of a pyrolysis type (for O determination). It should be understood, however, that the invention is applicable where the reactors 30*a*, 30*b* are of the same type of reactor 30*a*, 30*b* as each other or different to each other. For example, the reactors could both be of a combustion type or combustion/reduction type (e.g. for CHNS determination, which includes any subset thereof such as CHN or NCS determination). Such reactors are known in the art and comprise an oxidizing zone followed in the case of combustion/reduction reactors by a reduction zone downstream of the oxidizing zone as shown in FIGS. 4A-4D. Combustion or combustion/reduction reactors typically require a source of oxygen additional to the sample.

In another example, one of the reactors 30a, 30b could be of the combustion or combustion/reduction type and the other of the reactors 30a, 30b could be of a pyrolysis type (e.g. for O determination), which typically operates without a source of oxygen other than the sample. Such configurations are also shown in FIGS. 4A-4D. In a further example, both reactors could be of a pyrolysis type. Both types of reactors are housed in a furnace and in operation held at high temperature e.g. 900-1100 degree C. (for this reason, the conditions experienced by the reference gas may largely match those experienced by the carrier gas).

FIGS. 4A, 4B, 4C, and 4D, show possible configurations of reactors 30a, 30b to be used in the elemental analyzer.

Figure 4A:
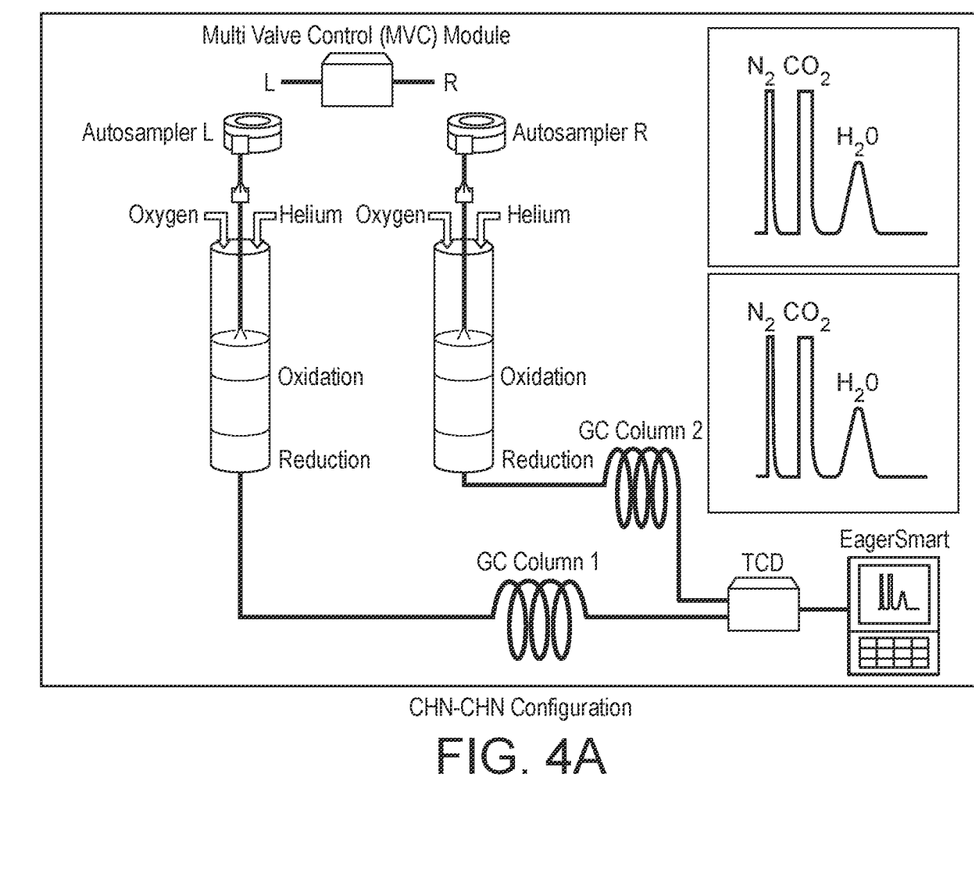
FIGS. 4A-4D show a schematic representation of some of the available configurations of reactors.

FIG. 4A shows that for an elemental analyzer arranged for CHN determination in each channel of the thermal conductivity detector 10, each reactor 30a, 30b may be configured for oxidation and reduction. Such reactors 30a may each require a supply of oxygen and carrier gas (e.g., helium).

Figure 4B:
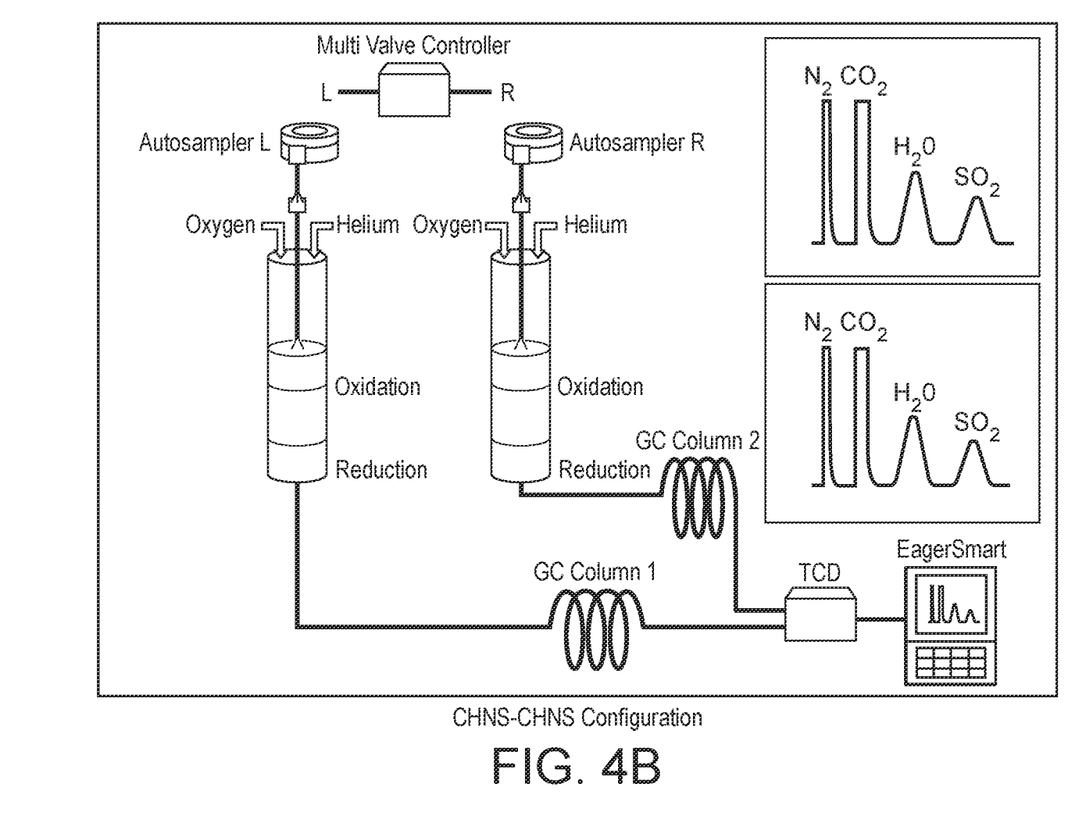

FIG. 4B shows that for an elemental analyzer arranged for CHNS determination in one channel of the thermal conductivity detector 10 and CHNS determination in the other channel of the thermal conductivity detector 10, each reactor 30a, 30b may be configured for oxidation and reduction. Such reactors 30 may each require a supply of oxygen and carrier gas (e.g., helium).

Figure 4C:
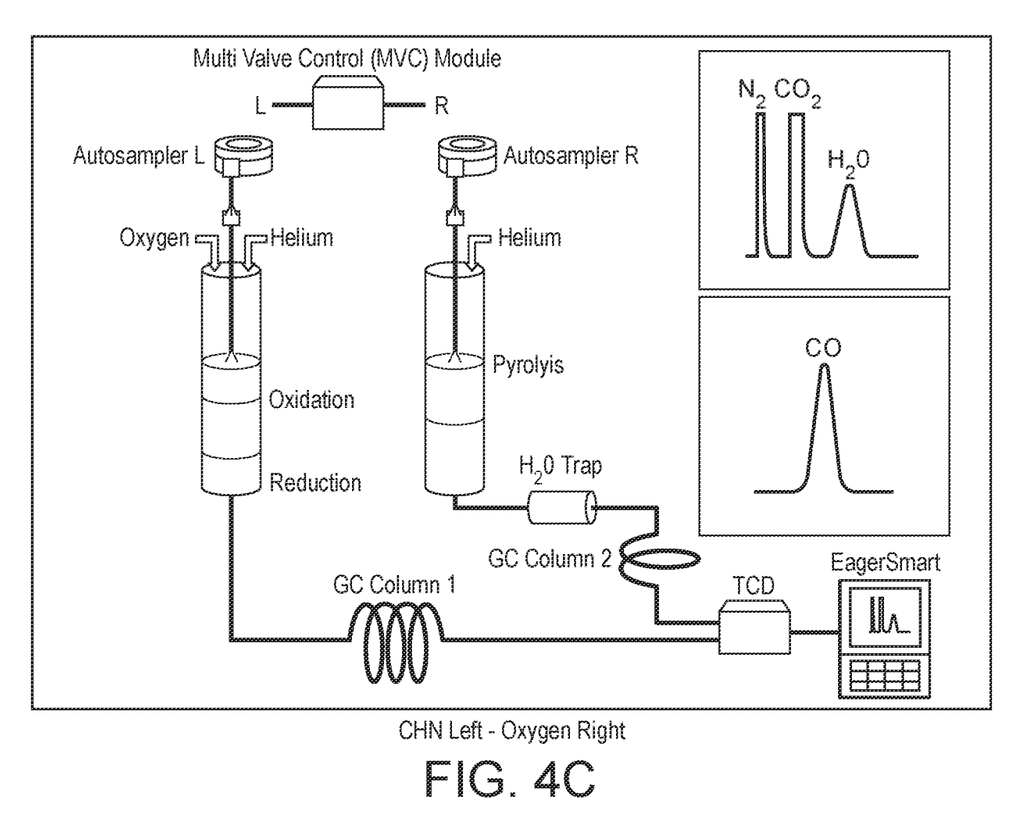

FIG. 4C shows that for an elemental analyzer arranged for CHN determination in one channel of the thermal conductivity detector 10 and O determination in the other channel of the thermal conductivity detector 10, one reactor 30a, 30b may be configured for oxidation and reduction and the other for pyrolysis. The pyrolysis configured reactor 30b would not require a supply of oxygen but does require a carrier gas flow (e.g., helium). The oxidation and reduction reactor 30a would require a supply of oxygen and carrier gas (e.g., helium).

Figure 4D:
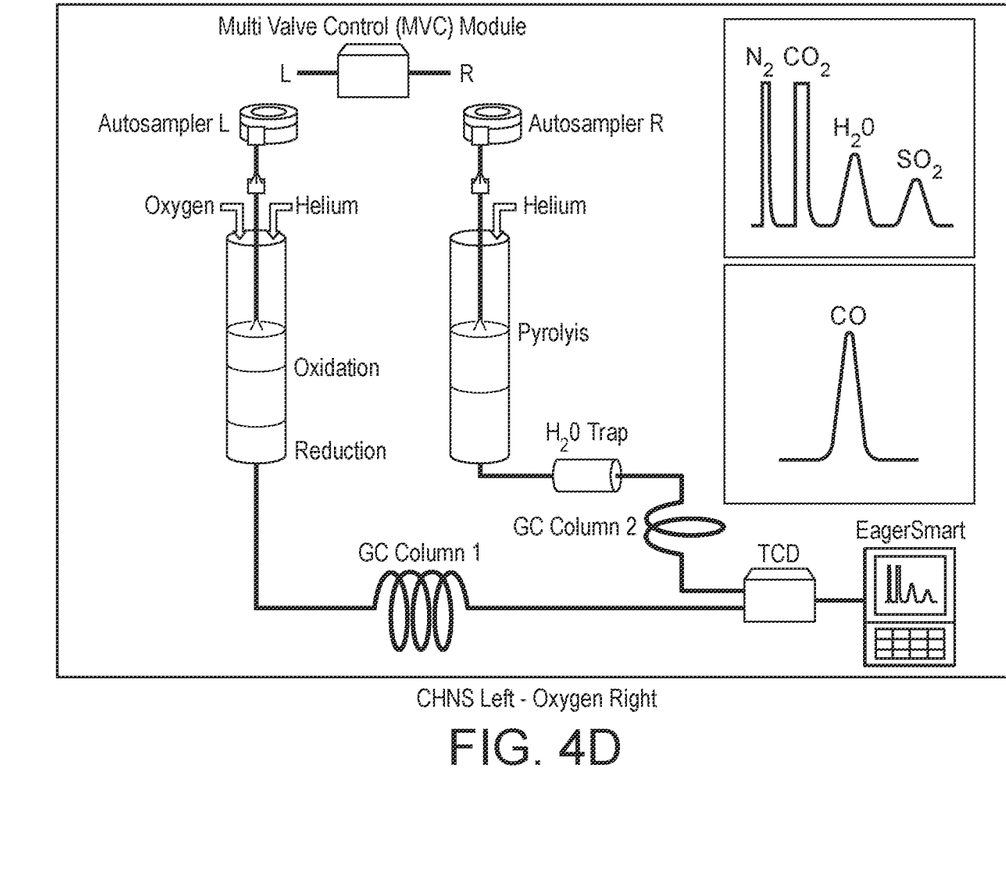

FIG. 4D shows that for an elemental analyzer arranged for CHNS determination in one channel of the thermal conductivity detector 10 and O determination in the other channel of the thermal conductivity detector 10, one reactor 30a, 30b may be configured for oxidation and reduction and the other for pyrolysis. The pyrolysis configured reactor 30b would not require a supply of oxygen but does require a carrier gas flow (e.g., helium). The oxidation and reduction reactor 30a would require a supply of oxygen and carrier gas (e.g., helium).

In FIGS. 4A-D, it should be noted that the provision of helium and oxygen is shown in a schematic form. It is not intended to imply that these must necessarily be supplied by different paths. As discussed below, both helium and oxygen may be supplied along a single conduit.

The valve system 80, 100 may be a single valve unit, or a distributed set of valves. In the preferred embodiment shown in FIGS. 2A-C, there are two main sets of valves of the valve system 80, 100; a supply valve system 80, and a control valve system 100. The control valve system 100 may, optionally, be divided as a first control valve system 105 and a second control valve system 110. The first control valve system 105 comprises four ports 100A, 100B, 100C, 100D.

The source of gases 70 may include a source of a first gas 70a and a source of a second gas 70b. Preferably, the source of gases 70 may include a source of a third gas 70c.

In some embodiments, the first gas 70a is helium and the second gas 70b is oxygen. The helium can be used as a carrier gas in normal modes of operation, for example, in which a sample is delivered to a reactor. The oxygen can be delivered to the combustion/reduction reactor to promote oxidation of the sample.

In configurations in which oxygen is needed in a reactor 30a, 30b, this is typically provided by switching the carrier gas supply from the first gas 70a, which may be a normal carrier gas such as helium, to the second gas 70b (which in that example would be oxygen) for a predetermined period of time (e.g., around five seconds) or a controlled time (e.g. as described in EP 1061366 A2). In this way, oxygen is provided via the carrier supply conduit 4.

In some embodiments, the third gas 70c is nitrogen or argon.

The thermal conductivity detector 10 has two channels along which gas can flow, a first channel 15 and a second channel 13. For example, in each channel may be a resistive element, and the relative thermal conductivity of the resistive elements may be measured in the manner known in the art. The first channel 15 has an inlet 14 and an outlet 18. The second channel 13 has an inlet 12 and an outlet 16. The first and second channels 15, 13 of the thermal conductivity detector 10 are comparable, and so one can be used as a measurement channel and the other as a reference channel, or vice versa.

The first and second gases 70a, 70b (or, in optional embodiments, the third and second gases 70c, 70b, as explained below) are delivered via a pressure regulator 60 to a valve system 80. Preferably, the first gas 70a (or third gas 70c) is delivered via a first pressure regulator 62 to a first inlet 82 of the valve system 80, and the second gas 70b is delivered via a second pressure regulator 64 to a second inlet 84 of the valve system 80.

The valve system 80 is arranged to provide a source of carrier gas to a carrier supply conduit 4 and provide a source of reference gas to a reference supply conduit 2. A preferred valve system 80 comprises a plurality of two-way valves that in combination can: supply the first gas 70a as the reference gas; and supply either of the first gas 70a or the second gas 70b as the carrier gas.

Preferably, a variable or proportional valve 86 is provided to meter a flow of the first gas 70a along the reference supply conduit 2.

Preferably, a set of valves 85 is provided to meter a flow of either the first gas 70a or the second gas 70b along the carrier supply conduit 4.

A valve 85b may be provided to connect a selected one (and only one) of the first inlet 82 and second inlet 84 of the valve system 80 with the carrier supply conduit 4. In the case in which the second gas 70b is oxygen, it is this valve that may be used to provide the predetermined or controlled quantity of oxygen to the reactor at the required time for oxidizing a sample.

A variable valve 86 may be provided to meter a flow of the selected gas along the carrier supply conduit 4.

The valve system 80 additionally comprises a variable valve 87 for directing gas received from the second channel 13 of the thermal conductivity detector 10 to a sampler port 21a of the first auto-sampler 20a. The valve system 80 additionally comprises a variable valve 88 for directing gas received from the first channel 15 of the thermal conductivity detector 10 to a sampler port 21b of the second auto-sampler 20b.

The auto-samplers 20a, 20b each have a store 24a, 24b, which may be loaded with one or more samples of materials to be delivered to the reactors 30a, 30b.

Each auto-sampler 20a, 20b has a delivery inlet 22a, 22b and a delivery outlet 23a, 23b.

Each auto-sampler 20a, 20b communicates a flow of gas received at the delivery inlet 22a, 22b to the delivery outlet 23a, 23b, and delivers into that flow a sample of material from the store 24a, 24b.

Two flow paths are provided. A first flow path includes, in series, the first port 100A of the control valve system 100, the first auto-sampler 20a (via the delivery inlet 22a and the delivery outlet 23a), the first reactor 30a, the first chromatography column 40a, and the first channel 15 of the thermal conductivity detector 10. A second flow path includes, in series, the third port 100C of the control valve system 100, the second auto-sampler 20b (via the delivery inlet 22b and the delivery outlet 23b), the second reactor 30b, the adsorption (or absorption) trap 50b, the second chromatography column 40b, and the second channel 13 of the thermal conductivity detector 10.

Optionally, a further adsorption (or absorption) trap 50a may be provided between the first reactor 30a and the first chromatography column 40a. It should also be understood that the adsorption (or absorption) trap 50b itself may be omitted in other embodiments, for example where O determination is not performed via the second reactor 30b.

The valve system 80, 100 (preferably, specifically the control valve system 100, and more preferably, specifically the second control valve system 110) may be configured to communicate with the source of the first gas 70a and the source of the third gas 70c, and output a gas selected from the first or third gases 70a, 70c. This selected gas forms the supply to the first regulator 62. Preferably, a three-way valve 112 is provided for this purpose.

The valve system 80, 100 (preferably, specifically the control valve system 100, and more preferably, specifically the first control valve system 105) may be configured to control the connectivity of the four ports 100A, 100B, 100C, 100D.

Preferably, a flow of gas received at the second port 100B is directed to one of the first and third ports 100A, 100C, while a flow of gas received at the fourth port 100D is directed to the other of the first and third ports 100A, 100C. In that way, the two input gas flows received at the second and fourth ports 100B, 100D, can be switched between the first and third ports 100A, 100C.

The flow of gas received at the second port 100B is directed to one of the first and third ports 100A, 100C, via an arrangement of one or more switchable valves. Similarly, the flow of gas received at the fourth port 100D is directed to the other of the first and third ports 100A, 100C via an arrangement of one or more switchable valves. In a most preferred embodiment, a set of four binary valves 105a, 105b, 105c, 105d is used for this purpose. Each binary valve switches between an open state (in which fluid may pass therethrough) and a closed state (in which fluid may not pass therethrough). The first port 100A is in communication with the output of the first and fourth 105a, 105d binary valves. The second port 100B is in communication with the input of the first and second 105a, 105b binary valves. The third port 100C is in communication with the output of the second and third 105b, 105c binary valves. The fourth port 100D is in communication with the input of the third and fourth 105c, 105d binary valves. The binary valves are preferably solenoid valves.

Figure 3:
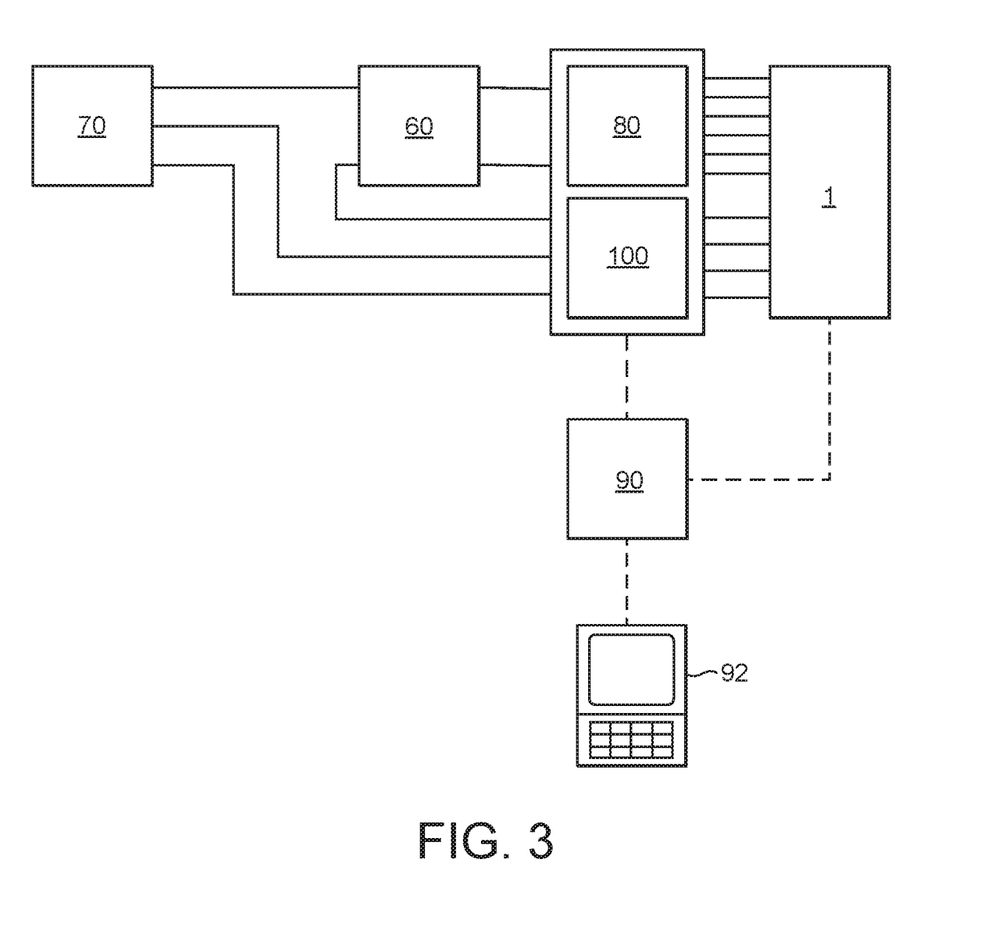
FIG. 3 shows a schematic overview of the embodiment of FIGS. 2A-C.

As shown in FIG. 3, preferably a controller 90 is provided. The controller 90 is arranged to operate the elemental analyzer 1. The controller 90 may additionally be programmed to control one or more (and preferably all) of: the supply valve system 80; the control valve system 100; the first valve system 105; and/or the second valve system 110.

The controller 90 may comprise, or as depicted, be connected to an interface 92. The user may provide, via the interface 92, an input that is stored in the controller 90 as a schedule of modes of operation. The controller 90 may be initiated to control the schedule of modes of operation. The controller 90 may comprise a computer processor. A computer program, when executed by the processor, enables control of the elemental analyzer 1 so as to operate in accordance with the modes of operation.

Preferably, when oxygen is the second gas 70b, the controller 90 is arranged to control the supply valve system 80 (via, for example, valves 85b and 85c) to deliver a predetermined quantity of oxygen into the carrier supply conduit 4. Such predetermined quantities can be programmed into the controller 90 as part of the schedule.

In a first mode of operation:
The controller 90 commands the second control valve system 110 to supply the first gas 70a to the supply valve system 80.
The controller 90 commands the supply valve system 80 to supply the first gas 70a to the carrier supply conduit 4.
The controller 90 commands the supply valve system 80 to supply the first gas 70a to the reference supply conduit 2.
The controller 90 commands the first control valve system 105 to connect the carrier supply conduit 4 via port 100B and port 100A to the first auto-sampler 20a.
The controller 90 commands the first auto-sampler 20a to deliver a sample into the first reactor 30a. The sample is delivered in the flow of gas provided by the control valve system 105.
The first reactor 30a delivers one or more reaction products to the first channel of the thermal conductivity detector 10.
The controller 90 commands the control valve system 105 to connect the reference supply conduit 2 via port 100D and port 100C to the second auto-sampler 20b, which does not deliver a sample.
The second auto-sampler 20b delivers reference gas to the second channel of the thermal conductivity detector 10 via the second reactor 30b, which does not receive a sample.

Not only does the reference gas provide a reference measurement in the TCD but the reference gas keeps the whole second flow path clean while the first flow path is being used for sample analysis and/or until the controller 90 commands the valve system 100 to switch flow paths.

In a second mode of operation:
The controller 90 commands the second control valve system 110 to supply the first gas 70a to the supply valve system 80.
The controller 90 commands the supply valve system 80 to supply the first gas 70a to the carrier supply conduit 4.
The controller 90 commands the supply valve system 80 to supply the first gas 70a to the reference supply conduit 2.
The controller 90 commands the first control valve system 105 to connect the carrier supply conduit 4 via port 100B and port 100C to the second auto-sampler 20b.

The controller 90 commands the second auto-sampler 20*b* to deliver a sample into the second reactor 30*b*. The sample is delivered in the flow of gas provided by the control valve system 105.

The second reactor 30*b* delivers one or more reaction products to the second channel of the thermal conductivity detector 10.

The controller 90 commands the control valve system 105 to connect the reference supply conduit 2 via port 100D and port 100A to the first auto-sampler 20*a*, which does not deliver a sample.

The first auto-sampler 20*a* delivers reference gas to the first channel of the thermal conductivity detector 10 via the first reactor 30*a*, which does not receive a sample.

In a third mode of operation:

The controller 90 commands the second control valve system 110 to supply the first gas 70*a* to the supply valve system 80.

The controller 90 commands the supply valve system 80 to supply the first gas 70*a* to the carrier supply conduit 4.

The controller 90 commands the supply valve system 80 to supply the first gas 70*a* to the reference supply conduit 2.

The controller 90 commands the first control valve system 105 to connect the carrier supply conduit 4 via port 100B and port 100A to the first auto-sampler 20*a*.

The controller 90 commands the first auto-sampler 20*a* to deliver a sample into the first reactor 30*a*. The sample is delivered in the flow of gas provided by the control valve system 105.

The controller 90 commands the supply valve system 80 to supply the second gas 70*b* (preferably, oxygen) to the carrier supply conduit 4 for a predetermined or controlled period of time following which the controller 90 commands the supply valve system 80 to again supply the first gas 70*a* to the carrier supply conduit 4.

The sample is reacted within the first reactor 30*a* in the presence of the second gas 70*b*.

The first reactor 30*a* delivers one or more reaction products to the first channel of the thermal conductivity detector 10.

The controller 90 commands the control valve system 105 to connect the reference supply conduit 2 via port 100D and port 100C to the second auto-sampler 20*b*, which does not deliver a sample.

The second auto-sampler 20*b* delivers reference gas to the second channel of the thermal conductivity detector 10 via the second reactor 30*b*, which does not receive a sample.

In a fourth mode of operation:

The controller 90 commands the second control valve system 110 to supply the first gas 70*a* to the supply valve system 80.

The controller 90 commands the supply valve system 80 to supply the first gas 70*a* to the carrier supply conduit 4.

The controller 90 commands the supply valve system 80 to supply the first gas 70*a* to the reference supply conduit 2.

The controller 90 commands the first control valve system 105 to connect the carrier supply conduit 4 via port 100B and port 100C to the second auto-sampler 20*b*.

The controller 90 commands the second auto-sampler 20*b* to deliver a sample into the second reactor 30*b*. The sample is delivered in the flow of gas provided by the control valve system 105.

The controller 90 commands the supply valve system 80 to supply the second gas 70*b* (preferably, oxygen) to the carrier supply conduit 4 for a predetermined or controlled period of time following which the controller 90 commands the supply valve system 80 to again supply the first gas 70*a* to the carrier supply conduit 4.

The sample is reacted within the second reactor 30*b* in the presence of the second gas 70*b*.

The second reactor 30*b* delivers one or more reaction products to the second channel of the thermal conductivity detector 10.

The controller 90 commands the control valve system 105 to connect the reference supply conduit 2 via port 100D and port 100A to the first auto-sampler 20*a*, which does not deliver a sample.

The first auto-sampler 20*a* delivers reference gas to the first channel of the thermal conductivity detector 10 via the first reactor 30*a*, which does not receive a sample.

In a fifth mode of operation:

The controller 90 commands the second control valve system 110 to supply the third gas 70*c*, not the first gas 70*a* to the supply valve system 80.

The controller 90 commands the supply valve system 80 to supply the third gas 70*c* to the carrier supply conduit.

The controller 90 commands the supply valve system 80 to supply the third gas 70*c* to the reference supply conduit.

The controller 90 commands the control valve system 105 to connect the carrier supply conduit 4 to one of the auto-samplers 20*a*, 20*b*, which is not activated.

The third gas 70*c* is carried from the first auto-sampler 20*a* to the first channel of the thermal conductivity detector 10 via the first reactor 30*a*, which is not activated.

The controller 90 commands the control valve system 105 to connect the reference supply conduit 2 to the other of the auto-samplers 20*a*, 20*b*, which is not activated.

The third gas 70*c* is carried from the second auto-sampler 20*b* to the second channel of the thermal conductivity detector 10 via the second reactor 30*b*, which is not activated.

The fifth mode of operation enables a change of the carrier gas in an automatic way so that, for example, the user can use helium as carrier gas when analysis of samples is being performed but when the instrument is placed in a Stand-By condition, for example overnight, the controller automatically commands the control valve system to switch over the carrier gas from helium to a cheaper standby gas such as nitrogen or argon. When the instrument is placed back to operation mode from stand-by, the controller may automatically command the control valve system to switch the carrier gas back to helium. This allows the user to reduce the cost per analysis as nitrogen, for example is considerably cheaper than helium.

In a preferred embodiment, a schedule may include one or more of the first to fourth modes of operation and, optionally, the fifth mode of operation. For example, the schedule may commence with switching from the fifth mode of operation sequentially through one or more of the first to fourth modes of operation and then conclude with switching to the fifth mode of operation.

The user may input any one or more of the following information, for example via the interface 92, to enable the controller to operate the elemental analyzer according to a predetermined schedule:

The type of gas to use.

For example the user may choose between helium for the first to fourth operation modes, or either $N_2$ or Ar for the fifth operation mode. Helium is the carrier gas used for the analysis while nitrogen or argon can be used for saving helium when the instrument is not being used for a prolonged period of time, for example, overnight or on weekends.

The equilibrium time when switching back to helium (min).

For example the user may select the time required for equilibrating the system when the gas supply switches back from argon to helium. For instance, a time may be chosen from 15 minutes to 75 minutes, such as in steps of 15 minutes.

The reactor (first or second) to use for analysis.

For example the user may select the reactor (i.e. the flow path/channel) according to the determination to be done (for example CHNS determination, or O determination). Preferably, the polarity of the TCD signal is set according to the channel selected: for example positive polarity for first reactor determinations, and negative polarity for second reactor determinations.

The equilibrium time when switching the channel in use (min).

For example the user may select the time required for equilibrating the system when the channel switches from first to second reactor (CHNS to O) or vice-versa. For instance, a time may be chosen from 5 minutes to 75 minutes, such as in steps of 5 minutes.

The analysis system is preferably an organic elemental analysis (OEA) system (such as a system determining the presence and quantity of one or more elements in an organic sample, for example elements selected from C, H, N, S and O), or an isotope ratio mass spectrometry (IRMS) elemental analysis system.

It has been mentioned above in the context of the described preferred embodiment that the analysis system may be set up in a CHNS/O configuration but the analyzer for example may be configured for CHN/CHNS or CHNS/CHNS or CHN/CHN or NCICHNS or CHNIS or N/CHNS etc.

The analysis system according to the invention enables the use of two autosamplers with two reaction channels in an automatic manner, i.e. without manual intervention to modify the hardware or software. Thereby, the invention makes it much easier to plan and implement a schedule of laboratory activity. The analyzer may even work without the user present and the analyzer may work in a continuous manner, day and night.

As an example, the user can plan to analyse, for example, 50 samples in a CHNS determination mode (on the first reactor) followed by, for example, 30 samples in an Oxygen determination mode (on the second reactor) in an automatic, time-saving and labour-saving way. The analysis instrument thus analyses the 50 sample in CHNS mode and, at the end of that run, automatically switches to the other reaction channel to evaluate the other batch of 30 samples.

Although the invention has been exemplified by reference to an embodiment including two autosamplers and a respective two reactors, it will be appreciated that the invention may be employed in a system comprising three or more autosamplers and/or three or more reactors.

Figure 5:
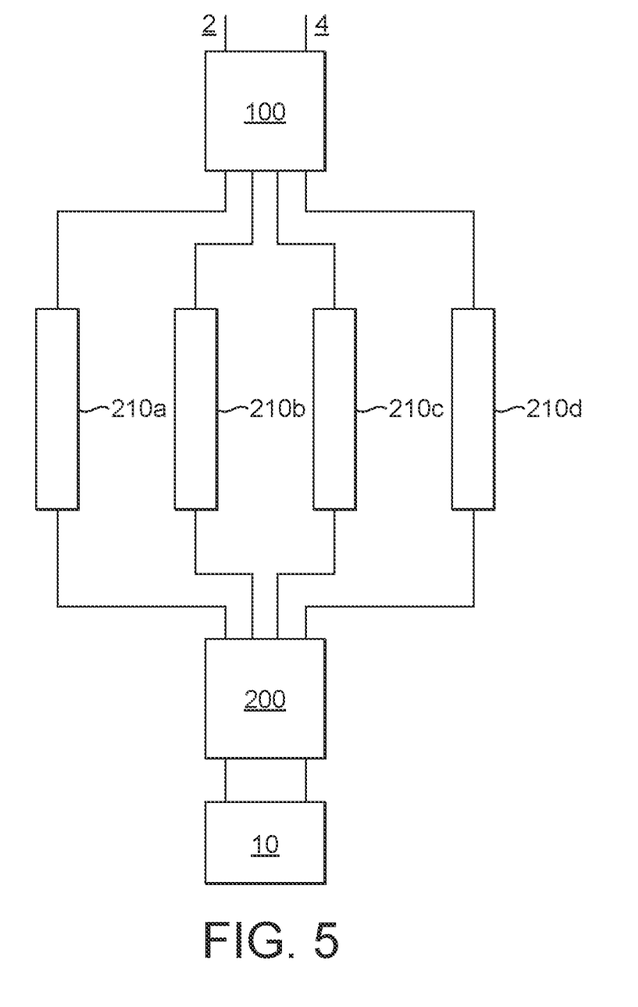
FIG. 5 schematically represents an alternative embodiment of an elemental analyzer in accordance with the invention.

As shown in FIG. 5, this may be achieved by providing an output valve system 200 (which may be a sub-system of valve system (80, 100) described above) at the output of the reactors 30 or, more preferably, at the output of the chromatography columns 40.

For example, more than two flow paths 210a, 210b, 210c, 210d may be provided. Each flow path 210 may be supplied by a port of the control valve system 100, and will supply a port of the output valve system 200.

Each flow path 210 may include, in series, an auto-sampler 20 (via a delivery inlet 22a and a delivery outlet 23a), a reactor 30 and, optionally, a chromatography column 40. The flow paths 210 work in the manner described above.

The controller 90 may be arranged to control the output valve system 200.

For example, at any one time, the controller 90 may connect one of the flow paths 210 so as to be supplied by the carrier supply conduit 4 and to supply one channel of the thermal conductivity detector 10. Simultaneously, the controller 90 may connect the remaining flow paths 210 so as to be supplied by the reference supply conduit 2 and to supply the other channel of the thermal conductivity detector 10.

Alternatively, at any one time, the controller 90 may connect more than one of the flow paths 210 so as to be supplied by the carrier supply conduit 4 and to supply one channel of the thermal conductivity detector 10, but the controller 90 will command a single auto-sampler 20 in only one of those flow paths to deliver a sample. Simultaneously, the controller 90 may connect the remaining flow paths 210 so as to be supplied by the reference supply conduit 2 and to supply the other channel of the thermal conductivity detector 10.

What is claimed is:

1. An analysis system for analysing the constituents of a sample of material, the system comprising:
   a reference supply conduit for supplying a source of a first gas;
   a carrier supply conduit for supplying a source of the first or a second gas;
   first and second reactors;
   a first auto-sampler for providing one or more samples of material, the first auto-sampler having an inlet for receiving gas and an outlet for providing the received gas and a sample to the first reactor;
   a second auto-sampler for providing one or more samples of material, the second auto-sampler having an inlet for receiving gas and an outlet for providing the received gas and a sample to the second reactor;
   a thermal conductivity detector having first and second channels for identifying the relative conductivity of the gases in each channel,
   characterized in that:
      the system further comprises a valve system arranged to control the flow of gas from the supply conduits to the inlets of the first and second auto-samplers;
      the analysis system has a first mode of operation in which:
         the valve system connects the carrier supply conduit with the first auto-sampler;
         the first auto-sampler delivers the received gas and a sample to the first reactor;
         the first reactor delivers at least one reaction product to one channel of the thermal conductivity detector; and
         the valve system connects the reference supply conduit to the other channel of the thermal conductivity detector; and
      the analysis system has a second mode of operation in which:

the valve system connects the carrier supply conduit with the second auto-sampler;

the second auto-sampler delivers the received gas and a sample to the second reactor;

the second reactor delivers at least one reaction product to one channel of the thermal conductivity detector; and the valve system connects the reference supply conduit to the other channel of the thermal conductivity detector.

2. The analysis system of claim 1, wherein the first channel of the thermal conductivity detector is arranged to be in communication with the first reactor and thereby arranged to receive a reaction product therefrom, the second channel of the thermal conductivity detector is arranged to be in communication with the second reactor and thereby arranged to receive a reaction product therefrom.

3. The analysis system of claim 1, wherein:
in the first mode of operation:
the first reactor delivers a reaction product to the first channel of the thermal conductivity detector; and
the valve system connects the reference supply conduit to the second channel of the thermal conductivity detector; and
in the second mode of operation:
the second reactor delivers a reaction product to the second channel of the thermal conductivity detector; and
the valve system connects the reference supply conduit to the first channel of the thermal conductivity detector.

4. The analysis system of claim 1, comprising a first source of gas and a second source of gas, wherein the valve system is arranged to connect the carrier supply conduit to one of: the first source of gas; or the second source of gas.

5. The analysis system of claim 4, wherein the first source of gas comprises a first source of carrier gas and a source of a stand-by gas, and wherein the valve system is arranged to connect one or both of the reference supply conduit and/or the carrier supply conduit to one of: the first source of carrier gas; or the source of stand-by gas.

6. The analysis system of claim 5, wherein the analysis system has a third mode of operation in which:
the source of stand-by gas is in communication with both the reference supply conduit and the carrier supply conduit;
the valve system connects the reference supply conduit with one of the auto-samplers, one of the reactors, and one channel of the thermal conductivity detector; and
the valve system connects the carrier supply conduit with the other of the auto-samplers; the other of the reactors, and the other channel of the thermal conductivity detector.

7. The analysis system of claim 1, wherein:
the analysis system has a third mode of operation in which:
the valve system connects the carrier supply conduit with the first auto-sampler;
the first auto-sampler delivers the received gas and a sample to the first reactor;
the valve system supplies a first gas to the carrier supply conduit, then supplies a second gas to the carrier supply conduit for a predetermined or controlled period of time, and then again supplies the first gas to the carrier supply conduit;
the first reactor delivers at least one reaction product to one channel of the thermal conductivity detector; and the valve system connects the reference supply conduit to the other channel of the thermal conductivity detector; and the analysis system has a fourth mode of operation in which:
the valve system connects the carrier supply conduit with the second auto-sampler;
the second auto-sampler delivers the received gas and a sample to the second reactor;
the valve system supplies a first gas to the carrier supply conduit, then supplies a second gas to the carrier supply conduit for a predetermined or controlled period of time, and then again supplies the first gas to the carrier supply conduit;
the second reactor delivers at least one reaction product to one channel of the thermal conductivity detector; and
the valve system connects the reference supply conduit to the other channel of the thermal conductivity detector.

8. The analysis system of claim 7, wherein:
the analysis system has a fifth mode of operation in which:
the valve system supplies a third gas to the carrier supply conduit and the reference supply conduit;
the first and second auto-samplers do not deliver any samples to the reactors; and
the reactors deliver the received gas to one channel of the thermal conductivity detector.

9. The analysis system of claim 8, further comprising a programmable controller arranged to be programmed with a predetermined schedule of the operating modes and thereby operate the analysis system according to that schedule.

10. The analysis system of claim 9, wherein the programmable controller (90) is programmed with a predetermined schedule that defines a sequence of the operating modes.

11. The analysis system of claim 10, wherein the predetermined schedule defines a sequence of operating modes concluding with the fifth operating mode.

12. The analysis system of claim 10, wherein the predetermined schedule defines a sequence of operating modes including one of the third and fourth operating mode and also defines the predetermined or controlled periods of time in which the second gas is delivered.

13. The analysis system of claim 1, wherein the valve system is arranged to:
connect the output of the first reactor to a first of the channels of the thermal conductivity detector and simultaneously connect the output of the second reactor to a second of the channels of the thermal conductivity detector; or
connect the output of the first reactor to the second of the channels of the thermal conductivity detector and simultaneously connect the output of the second reactor to the first of the channels of the thermal conductivity detector.

14. The analysis system of claim 1, wherein:
more than two reactors are provided;
the valve system is arranged to connect the carrier supply conduit to at least one of the reactors and connect the at least one of the reactors with a first of the channels of the thermal conductivity detector; and
the valve system is arranged to connect the reference supply conduit to the other reactors and connect those other reactors with a second of the channels of the thermal conductivity detector.

15. The analysis system of claim 14, wherein:
more than two auto-samplers are provided;

the valve system is arranged to connect the carrier supply conduit to at least one of the auto-samplers and connect the at least one of the auto-samplers with a first of the channels of the thermal conductivity detector; and the valve system is arranged to connect the reference supply conduit to the other auto-samplers and connect those other auto-samplers with a second of the channels of the thermal conductivity detector.

\* \* \* \* \*